United States Patent [19]

Gotoh et al.

[11] Patent Number: 5,017,730

[45] Date of Patent: May 21, 1991

[54] PROCESS OF PREPARING BIS (TRIFLUOROMETHYLPHENYL) METHANOL

[75] Inventors: Yoshihiko Gotoh, Kamifukuoka; Toshikazu Kawai; Junji Negishi, both of Saitama, all of Japan

[73] Assignee: Central Glass Company, Limited, Ube, Japan

[21] Appl. No.: 491,969

[22] Filed: Mar. 12, 1990

[30] Foreign Application Priority Data

Mar. 27, 1989 [JP] Japan .................................. 1-74696

[51] Int. Cl.$^5$ ............................................. C07C 39/367
[52] U.S. Cl. .................................... 568/812; 568/715
[58] Field of Search ............................... 568/812, 814

[56] References Cited

FOREIGN PATENT DOCUMENTS

| 1086432 | 7/1976 | Japan | 568/814 |
| 1204147 | 9/1986 | Japan | 568/812 |

OTHER PUBLICATIONS

J. Org. Chem., vol. 49, pp. 409–413, (1984), by David Kelly et al.

*Primary Examiner*—Werren B. Lone
*Attorney, Agent, or Firm*—Fleit, Jacobson, Cohn, Price, Holman & Stern

[57] ABSTRACT

The invention provides a process for easily, efficiently and economically preparing bis(trifluoromethylphenyl)methanol from either toluoyl chloride or a trihalomethylbenzoyl chloride. First the starting compound is reacted with toluene in the presence of a strong acid catalyst such as a perfluoroalkylsulfonic acid to form a benzophenone derivative, $CX_3C_6H_4-CO-C_6H_4CH_3$, wherein X is H, F, Cl or Br. Next, by chlorination the benzophenone derivative is converted into $CY_3C_6H_4-CO-C_6H_4CCL_3$, wherein Y is F or Cl, and then the chlorinated intermediate is fluorinated into bis(trifluoromethyl)benzophenone. By reduction of carbonyl group of this benzophenone derivative the aimed compound is obtained.

10 Claims, No Drawings

PROCESS OF PREPARING BIS (TRIFLUOROMETHYLPHENYL) METHANOL

BACKGROUND OF THE INVENTION

This inventio relates to a process of preparing bis(trifluoromethylphenyl)methanol,

which is a compound useful as an intermediate material for medicines such as anti-arrhythmia drug, agricultural chemicals or liquid crystals.

It is known to synthesize bis(trifluoromethylphenyl)methanol by reaction of a substituted benzaldehyde with a Grignard reagent derived from phenylbromide. [J. Org. Chem., 49, 409–413 (1984)]

However, the reactants for this method cannot easily be obtained as industrial materials, and the yield of the aimed compound is too low for industrial employment of this method.

SUMMARY OF THE INVENTION

It is an object of the present invention to provide a process for preparing bis(trifluoromethylphenyl)methanol easily, efficiently and economically.

The present invention provides a process of preparing bis(trifluoromethylphenyl)methanol, the process comprising the steps of (a) reacting a compound represented by the general formula (1), viz. either toluoyl chloride or a trihalomethylbenzoyl chloride, with toluene in the presence of a strong acid catalyst to form a first benzophenone derivative represented by the general formula (2),

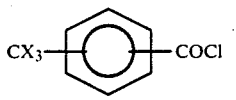

wherein X represents H, F, Cl or Br;

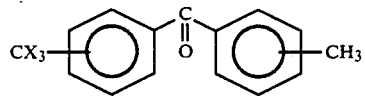

wherein X represents H, F, Cl or Br, (b) reacting the first benzophenone derivative with a chlorinating agent to form a second benzophenone derivative represented by the general formula (3),

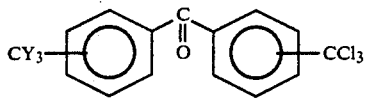

wherein Y represents F or Cl, (c) reacting the second benzophenone derivative with a fluorinating agent to form bis(trifluoromethyl)benzophenone,

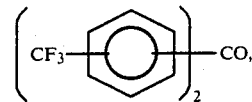

and (d) reacting the obtained bis(trifluoromethyl)benzophenone with a reducing agent to obtain bis(trifluoromethylphenyl)methanol by reduction of the carbonyl group.

In this process the step (a) is an acylation reaction of toluene using a strong acid catalyst, i.e. a Friedel-Crafts reaction. As the strong acid catalyst it is suitable to use a perfluoroalkylsulfonic acid. Toluene is used in a large excess so that unreacted toluene serves as a liquid medium for the reaction. Alternatively it is possible to carry out the reaction in another solvent in which the reactants are soluble.

For the chlorination at the step (b) it is suitable to use chlorine gas, and for the fluorination at the step (c) it is preferred to use hydrogen fluoride. As the reducing agent at the step (d) hydrogen gas is preferred.

The process according to the invention employs readily available and relatively inexpensive compounds as the starting materials, and each reaction in this process can easily be carried out under relatively mild conditions. This process is fairly high in the yield of bis(trifluoromethylphenyl)methanol on the basis of the starting compound of the general formula (1). By this process it is possible to prepare bis(trifluoromethylphenyl)methanol with the trifluoromethyl substitution at a desired position.

DESCRIPTION OF THE PREFERRED EMBODIMENTS

For the initial Friedel-Crafts reaction it is suitable to use a perfluoroalkylsulfonic acid as the catalyst, and it is preferred to use trifluoromethanesulfonic acid. The quantity of the catalyst is not strictly limited and may range from 0.1 to 100 mol % of the starting compound of the general formula (1), though the range of from 5 to 20 mol % is preferable. In the case of using an organic solvent other than toluene it is suitable to use hexane or 1,2-dichloroethane.

When, for example, p-trifluoromethylbenzoyl chloride is reacted with toluene the reaction product is a mixture of o-, m- and p-isomers of the general formula (2), but these isomers can be separated from each other by an ordinary method such as recrystallization.

The second step of the process is chlorinating the methyl group of the benzophenone derivative (2) (and also —CX$_3$ if —CX$_3$ is —CBr$_3$). From an industrial point of view it is preferred to use chlorine gas as the chlorinating agent. The chlorination is easily accomplished by dissolving the benzophenone derivative (2) in a chlorine-containing organic solvent such as carbon tetrachloride or 1,2-dichloroethane, adding a radical reaction initiator such as, for example, azobisisobutyronitrile or benzoyl peroxide and then blowing chlorine gas into the solution preferably at a temperature of about 60°–70° C.

At the next step for fluorination of trichloromethyl group the fluorinating agent can be selected from, for example, hydrogen fluoride, antimony pentafluoride, cobalt fluoride and silver fluoride. For industrial practice of the invention it is preferred to use hydrogen fluoride. It is suitable to perform the fluorination reaction by charging the chlorinated intermediate of the general formula (3), an organic solvent such as toluene, methylene chloride, chloroform or dichloroethane and hydrogen fluoride in an autoclave and heating the mixture at about 80°-140° C. while continuously or intermittently extracting hydrogen chloride gas formed by the reaction. The quantity of hydrogen fluoride is 1 to 10 times the theoretical quantity for complete fluorination of the trichloromethyl group(s) of the compound (3). Optionally, catalytic amount of antimony pentachloride is added to the reaction system for promoting the fluorinating reaction.

At the final step for the reduction of the carbonyl group of bis(trifluoromethyl)benzophenone, hydrogen gas is preferred as the reducing agent in industrial practice of the invention. As a hydrogenation catalyst usually a noble metal such as Pd, Pt or Rh is used. From an industrial point of view it is suitable to use a palladium-on-carbon catalyst. Usually the reduction reaction is carried out by dispersing bis(trifluoromethyl)benzophenone and the catalyst in an organic liquid medium preferably selected from alcohols such as methanol, ethanol and butanol and ethers such as ethyl ether and butyl ether and maintaining the dispersion in a hydrogen gas atmosphere at a pressure of 1 to 20 atm and at a temperature ranging from room temperature to about 100° C. For preventing the occurrence of hydrolysis during the reaction it is optional to add sodium hydroxide (e.g. 10% aqueous solution) amounting to 10-100 mol % of bis(trifluoromethyl)benzophenone.

The invention is further illustrated by the following nonlimitative examples.

EXAMPLE 1

1. Friedel-Crafts Reaction

In a glass reactor, a mixture of 600 ml of toluene and 22.5 g of trifluoromethanesulfonic acid were kept heated at 110° C., and, while stirring the mixture, 312.8 g of trifluoromethylbenzoyl chloride was dropped into the reactor so as to spend 5 hr in dropping the entire quantity. After that the heating and stirring were continued for 5 hr, and then 1.2 liter of hexane was added to cause precipitation of 4-trifluoromethyl-4'-methylbenzophenone in the form of platy crystals. The cystalline precipitate was collected by filtration, washed and dried. The dried product weighed 276 g (69% yield). From the filtrate, 111 g (28% yield) of 4-trifluoromethyl-2'-methylbenzophenone was obtained.

Analysis of the reaction products gave the following results.

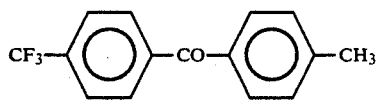

m.p.: 147° C.
$^1$H-NMR (ppm): 2.45 (s, 3H), 7.25–7.34 (m, 2H), 7.66–8.02 (m, 6H)
$^{19}$F-NMR (ppm): −63.52 (s)
IR: 1650 cm$^{-1}$ (C=O), 1130 cm$^{-1}$ (CF$_3$)

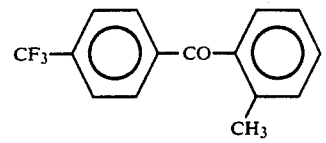

b.p.: 116° C./2 mmHg
$^1$H-NMR (ppm): 2.35 (s, 3H), 7.22–7.58 (m, 4H), 7.66–8.06 (m, 4H)
$^{19}$F-NMR (ppm): −63.61 (s)
IR: 1695 cm$^{-1}$ (C=O), 1150 cm$^{-1}$ (CF$_3$)

2. Chlorination

In a chlorination apparatus made of glass, 276 g of 4-trifluoromethyl-4'-methylbenzophenone prepared by the above Friedel-Crafts reaction was dissolved in 1.7 liter of carbon tetrachloride. The temperature of the solution was maintained at 65° C., and azobisisobutyronitrile (ABIN) was added so as to amount to 2 wt % of the dissolved material. Then chlorination reaction was carried out by blowing chlorine gas into the solution. After the reaction the solution was cooled to cause precipitation of crystals of 4-trifluoromethyl-4'-trichloromethylbenzophenone. The crystals were collected by filtration, washed and dried. The dried product weighed 380 g (99% yield). Analysis of the product gave the following results.

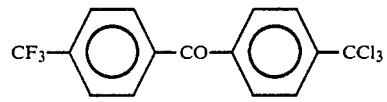

m.p.: 130° C.
$^1$H-NMR (ppm): 7.78–8.26 (m)
$^{19}$F-NMR (ppm): −63.58 (s)
IR: 1685 cm$^{-1}$ (C=O), 1170 cm$^{-1}$ (CF$_3$)

3. Fluorination

A stainless steel (SUS 316) autoclave was charged with 90 g of 4-trifluoromethyl-4'-trichlorobenzophenone, 180 ml of methylene chloride and 150 ml of hydrogen fluoride, and the temperature in the autoclave was maintained at 100°-130° C. for 30 hr to accomplish fluorination reaction. Whenever the internal pressure exceeded 25 atm, the autoclave was suitably relieved of pressure.

After the reaction the methylene chloride solution was poured into iced water and then washed with 5% aqueous solution of sodium hydroxide. The washed solution was concentrated to obtain 54 g of bis(p-trifluoromethyl)benzophenone as the reaction product.

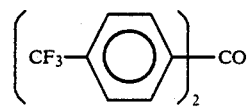

m.p.: 130° C.
$^1$H-NMR (ppm): 7.72–7.96 (m, J=8.6 Hz, J=4.8 Hz)
$^{19}$F-NMR (ppm): −63.63 (s)
IR: 1670 cm$^{-1}$ (C=O), 1150 cm$^{-1}$ (CF$_3$)

4. Reduction

The whole quantity (54 g) of the product of the above fluorination reaction was suspended in 170 ml of methanol. After adding 5.4 g of palladium-on-carbon catalyst (5 wt % Pd), the suspension was subjected to reduction in hydrogen gas atmosphere at normal pressure and at room temperature. The reduction reaction was continued for 3 days. After that the catalyst was removed by filtration, and the methanol was distilled out. The residual solid was dissolved in ethyl ether, and the ether solution was washed with saturated aqueous solution of sodium chloride, dried and concentrated to thereby obtain 49 g of bis(p-trifluoromethylphenyl)methanol (63% yield).

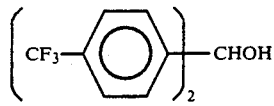

m.p.: 80° C.
$^1$H-NMR (ppm): 2.61 (s, 1H), 5.94 (s, 1H), 7.42–7.66 (m, J=8.5 Hz, J=4.7 Hz)
$^{19}$F-NMR (ppm): −63.14 (s)
IR: 3370 cm$^{-1}$ (OH), 1120 cm$^{-1}$ (CF$_3$)

EXAMPLE 2

In a glass reactor a mixture of 600 ml of toluene and 22.5 g of trifluoromethanesulfonic acid was kept heated at 110° C., and, while stirring the mixture, 231.9 g of toluoyl chloride was dropped into the reactor so as to spend 5 hr in dropping the entire quantity. After that the heating and stirring were continued for 4 hr, and then hexane was added to cause precipitation of crystalline 4,4'-dimethylbenzophenone, which weighed 151 g (48% yield) after drying.

The entire quantity of the obtained 4,4'-dimethylbenzophenone was put into a chlorination apparatus made of glass and dissolved in 1.5 liter of carbon tetrachloride. The solution was maintained at 65° C., and ABIN was added so as to amount to 2 wt % of the dissolved material, and chlorine gas was blown into the solution. After the chlorination reaction the solution was cooled to precipitate crystalline 4,4'-bis(trichloromethyl)benzophenone, which weighed 295 g (99% yield) after drying.

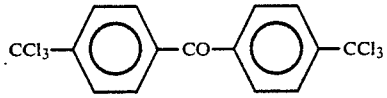

m.p.: 203° C.
$^1$H-NMR (ppm): 7.88–8.28 (m, J=78 Hz, J=12.6 Hz)
IR: 1660 cm$^{-1}$ (C=O)

Next, 200 g of 4,4'-bis(trichloromethyl)benzophenone, 500 ml of methylene chloride and 200 ml of hydrogen fluoride were charged in an autoclave and subjected to reaction at 110°–130° C. for 30 hr. After the reaction the methylene chloride solution was treated in the same manner as in Example 1 to thereby obtain bis(p-trifluoromethyl)benzophenone, which weighed 145 g (95% yield) after drying. The reduction of the fluorinated intermediate gave bis(p-trifluoromethylphenyl)methanol.

What is claimed is:

1. A process of preparing bis(trifluoromethylphenyl)methanol, comprising the steps of:
   (a) reacting a compound represented by the formula (1) with toluene at an elevated temperature in the presence of a perfluoroalkylsulfonic acid which serves as a strong acid catalyst to form a first benzophenone derivative represented by the formula (2),

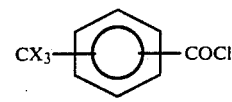

wherein X represents H, F, Cl or Br,

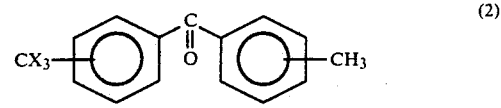

wherein X represents H, F, Cl or Br;
   (b) reacting said first benzophenone derivative with chlorine gas at a temperature in the range of from about 60° C. to about 70° C. to form a second benzophenone derivative represented by the formula (3),

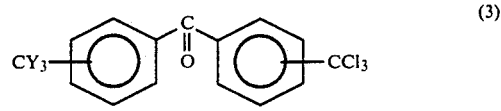

wherein Y represents F or Cl;
   (c) reacting said second benzophenone derivative with a fluorinating agent selected from the group consisting of hydrogen fluoride, antimony pentafluoride, cobalt fluoride and silver fluoride at a temperature in the range of from 80° C. to about 140° C. to form bis(trifluoromethyl)benzophenone; and
   (d) reacting said bis(trifluoromethyl)benzophenone with hydrogen gas at a pressure in the range of from about 1 atm to about 20 atm and at a temperature in the range of from room temperature to about 100° C. to form bis(trifluoromethylphenyl)methanol by reduction of the carbonyl group.

2. A process according to claim 1, wherein at step (a) an excess of toluene is used such that the excess toluene serves as a liquid medium for the reaction.

3. A process according to claim 1, wherein the reaction at step (a) is carried out in an organic solvent selected from the group consisting of hexane and 1,2-dichloroethane.

4. A process according to claim 1, wherein said strong acid catalyst is trifluoroalkylsulfonic acid.

5. A process according to claim 1, wherein the reaction at step (b) is carried out in a chlorine-containing organic solvent.

6. A process according to claim 5, wherein the reaction at step (b) is carried out in the presence of a radical reaction initiator.

7. A process according to claim 1, wherein the reaction at step (c) is carried out in an organic solvent.

8. A process according to claim 1, wherein the reaction at step (d) is carried out in an organic solvent.

9. A process according to claim 8, wherein the reaction at step (d) is carried out in the presence of a noble metal selected from the group consisting of Pd, Pt and Rh which serves as a hydrogen catalyst.

10. A process according to claim 1, wherein said elevated temperature in the step (a) is about 110° C.

* * * * *